(12) United States Patent
Osborne et al.

(10) Patent No.: US 7,799,942 B2
(45) Date of Patent: *Sep. 21, 2010

(54) PRODUCTION OF TEREPHTHALIC ACID DI-ESTERS

(75) Inventors: Vickie Haygood Osborne, Fall Branch, TN (US); Phillip Wayne Turner, Blountville, TN (US); Steven Leroy Cook, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/699,652

(22) Filed: Jan. 30, 2007

(65) Prior Publication Data

US 2007/0161815 A1 Jul. 12, 2007

Related U.S. Application Data

(63) Continuation-in-part of application No. 11/202,975, filed on Aug. 12, 2005, now Pat. No. 7,276,621.

(51) Int. Cl.
C07C 69/76 (2006.01)
(52) U.S. Cl. .......................................... 560/98; 569/98
(58) Field of Classification Search ............... 560/1, 560/99, 98; 569/98
See application file for complete search history.

(56) References Cited

U.S. PATENT DOCUMENTS

| | | | | |
|---|---|---|---|---|
| 1,944,887 | A * | 1/1934 | Graves ........................... | 554/1 |
| 2,124,605 | A | 7/1938 | Bousquet | |
| 2,459,014 | A * | 1/1949 | Lufkin et al. .................. | 560/98 |
| 2,479,066 | A * | 8/1949 | Gresham ..................... | 560/98 |
| 2,491,660 | A * | 12/1949 | Gresham ..................... | 560/99 |
| 2,579,329 | A * | 12/1951 | Martin ........................ | 568/764 |
| 2,802,861 | A * | 8/1957 | De Jonge et al. .............. | 560/98 |
| 2,975,209 | A | 3/1961 | Bos et al. | |
| 3,155,715 | A * | 11/1964 | Ardis et al. .................... | 560/98 |
| 3,250,801 | A * | 5/1966 | Stange et al. ................. | 560/95 |
| 4,380,677 | A * | 4/1983 | Kurek ........................ | 568/788 |
| 4,654,436 | A | 3/1987 | Lane et al. | |
| 5,138,025 | A * | 8/1992 | Mossman ................... | 528/298 |
| 5,326,864 | A | 7/1994 | Besemer et al. | |
| 5,391,770 | A | 2/1995 | Le Fur et al. | |
| 5,476,919 | A | 12/1995 | Schaeffer | |
| 5,532,495 | A | 7/1996 | Bloomquist et al. | |
| 5,571,387 | A * | 11/1996 | Marker et al. .................. | 203/41 |
| 5,585,527 | A * | 12/1996 | Marker ........................ | 203/18 |
| 6,350,895 | B1 | 2/2002 | Kurian | |
| 6,841,505 | B2 * | 1/2005 | Eng ............................ | 502/150 |
| 7,276,621 | B2 | 10/2007 | Cook et al. | |
| 2002/0028963 | A1 | 3/2002 | Gubisch et al. | |
| 2003/0232960 | A1 | 12/2003 | Adelman et al. | |
| 2004/0030175 | A1 | 2/2004 | Disteldorf et al. | |
| 2007/0161815 | A1 | 7/2007 | Osborne et al. | |

FOREIGN PATENT DOCUMENTS

| | | | |
|---|---|---|---|
| GB | 733 322 | | 7/1955 |
| GB | 878269 | * | 9/1961 |
| JP | 60 004151 | | 1/1985 |
| JP | 2001 031794 | | 2/2001 |
| JP | 2003 238479 | | 8/2003 |
| JP | 2004 30078 A | | 10/2004 |
| JP | 2005 120019 A2 | | 5/2005 |
| JP | 2003120019 A | * | 5/2005 |
| JP | 2005 306759 A2 | | 11/2005 |
| RU | 2 114 100 C1 | | 6/1998 |
| WO | WO 2007/021475 A2 | | 2/2007 |

OTHER PUBLICATIONS

Office Action date of mailing Jan. 10, 2008 received on the co-pending U.S. Appl. No. 11/732,236.
Mekhtiev, S. D. et al.; "Esterification of terephthalic and isophthalic acids by aliphatic alcohols"; Azerbaidzhanskii Khimicheskii Zhurnal; vol. 3; 1965; pp. 67-72.
Yoneda, Shigeo et al.; "Organic synthesis by use of inorganic salts. XII. Prepration of esters of carboxylic acids in dimethylformamide"; Kogyo Kagaku Zasshi; 69(4); 1966; pp. 641-643.
Roberts, Carleton W. et al.; The synthesis of and the dye-sensitized photoinitiated decompositions of monomolecular analogs of poly-(ethylene terephthalate); Clemson University Review of Industrial Management and Textile Science; 15(1); 1976; pp. 13-35.
Zeng, Chongyu; "Study on esterification rule in DOTP preparation"; XP0024138167 retrieved from STN Database accession No. 1995:468078; Chemical Abstracts Service, Columbus, Ohio.
Jiang, Pinping; "Synthesis of DOTP plasticizer by esterification"; XP002413816 retrieved from STN Database accession No. 1995:454573; Chemical Abstracts Service, Columbus, Ohio.
Meiqi, Fu; "A Technique of Producing Dioctyl Terephthalate and an Improvement in the Technique"; Tianjin Chemical Industry, China, vol. 20, No. 17, 2006.
Notification of Transmittal of the International Search Report and the Written Opinion of the International Searching Authority, or the Declaration date of mailing Feb. 16, 2007 received in the International Application No. PCT/US2006/028942.
Notification of Transmittal of the International Search Report and the Written Opinion of the International Searching Authority, or the Declaration date of mailing Jun. 25, 2008 received in the International Application No. PCT/US2008/008355.
Notification of Transmittal of the International Search Report and the Written Opinion of the International Searching Authority, or the Declaration date of mailing Jul. 2, 2008 received in the International Application No. PCT/US2008/000503.
Office Action date of mailing Jun. 11, 2008 received in U.S. Appl. No. 11/732,236.

(Continued)

*Primary Examiner*—Elvis O Price
(74) *Attorney, Agent, or Firm*—Brett L Nelson; Bernard J. Graves, Jr.

(57) ABSTRACT

Disclosed is a process for the preparation of a terephthalic acid di-ester by the esterification of terephthalic acid with an alcohol at elevated and normal temperature and pressure while the water of the reaction is removed from the reaction mixture via an inert gas or a column.

7 Claims, 2 Drawing Sheets

OTHER PUBLICATIONS

USPTO Board of Appeals and Interferences, *Ex parte Whalen II*, Appeal 2007-4423, decided Jul. 23, 2008.

Office Action date of notification Jun. 15, 2009 received in co-pending U.S. Appl. No. 12/174,291.

* cited by examiner

REACTOR AND COLUMN
FOR DOTP PRODUCTION

REACTOR AND COLUMN FOR DOTP PRODUCTION

PRODUCTION OF TEREPHTHALIC ACID DI-ESTERS

CROSS-REFERENCE TO RELATED APPLICATION

This application is a continuation-in-part of U.S. patent application Ser. No. 11/202,975, filed on Aug. 12, 2005, now U.S. Pat. No. 7,276,621 the disclosure of which is incorporated herein by reference in its entirety.

FIELD OF THE INVENTION

This invention pertains to the preparation of terephthalic acid di-esters from terephthalic acid (TPA).

BACKGROUND OF THE INVENTION

Terephthalic acid di-esters, such as Di-(2-ethylhexyl) terephthalate, also known as dioctyl terephthalate or DOTP, can be used as plasticizers in a variety of polymeric materials such as polyvinyl chloride. DOTP can be prepared by the titanate-catalyzed transesterification of dimethyl terephthalate (DMT) with 2-ethylhexanol (EH). Direct esterifications of TPA with EH under conditions similar to those used for the transesterification of DMT have produced slow reaction rates and sporadic problems with foaming. US-2002028963-A1 discloses an esterification process wherein water is removed by azeotropic distillation together with an alcohol. JP-60004151-A (JP-03004052-B) discloses the reaction of TPA and EH under elevated pressures and temperatures. JP-2001031794-A discloses the preparation of terephthalic acid esters by reacting at least one of C9-C 18 monohydric alcohol and 2-ethylhexanol with terephthalic acid. Water formed during the reaction was removed and the alcohol was separated and recirculated to the system. Finally, U.S. Pat. No. 5,532,495 discloses a multi-step esterification process that includes removing water and a portion of the alcohol reactant from the reaction mixture.

BRIEF SUMMARY OF THE INVENTION

An embodiment of the present invention concerns a process for the preparation of a terephthalic acid di-ester by the esterification of TPA with an alcohol at elevated pressure and temperature wherein the water of reaction and some of the alcohol are removed during the esterification process. This embodiment of the present invention therefore provides a process for the preparation of a terephthalic acid di-ester which comprises contacting TPA with an alcohol in the presence of a catalyst in a reaction zone wherein the alcohol comprises at least one of a $C_6$ to $C_{10}$ alcohol, the total pressure is maintained at about 1 to 4 bar gauge, the temperature is maintained at about 180° to 270° C., the alcohol:TPA mole ratio is maintained at about 2:1 to 2.5:1, and an inert gas is passed through the TPA/alcohol reaction mixture in the reaction zone to cause a mixture of water and alcohol to be removed from the reaction zone during the preparation of the terephthalic acid di-ester.

Another embodiment of the present invention concerns a process for the preparation of a terephthalic acid di-ester by the esterification of TPA with an alcohol at normal pressure and temperature. This embodiment comprises contacting TPA with an alcohol in the presence of a catalyst in a reaction zone, wherein the alcohol comprises at least one of a $C_6$ to $C_{10}$ alcohol, the pressure is at atmospheric pressure and the temperature is maintained at about 180° to 270° C. Moreover, this process employs a reactor fitted with a fractionation column for removing water.

The process according to the present invention provides the desired terephthalic acid diester product at good reaction rates with high conversions of the TPA reactant with no observable foaming problems.

DETAILED DESCRIPTION

Figure 1:
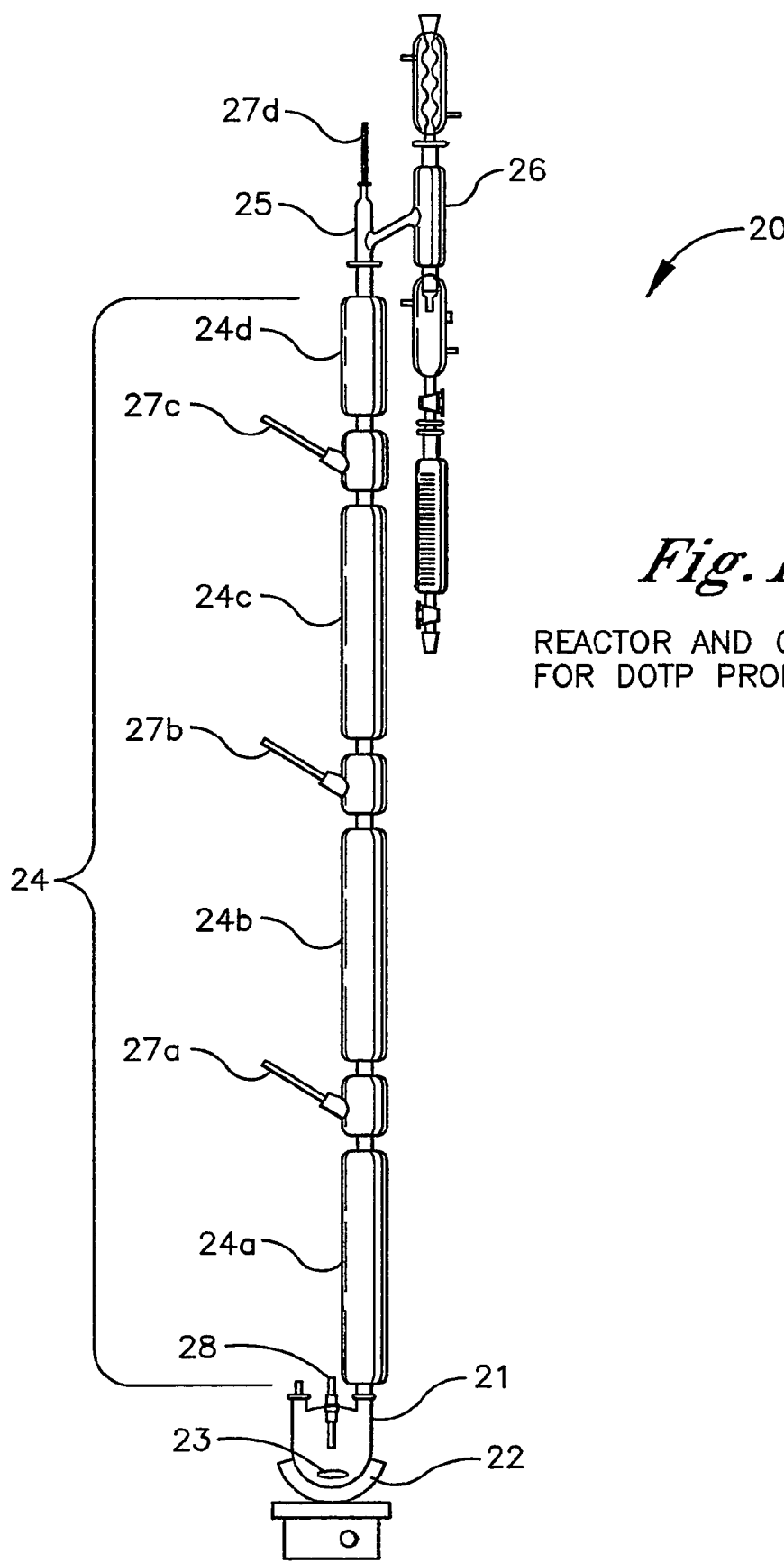
FIG. 1 shows a reactor and column useful with the process according to the present invention.

In a first embodiment, the esterification process of the present invention is carried out in a reaction zone comprising a pressure vessel while maintaining the alcohol:TPA mole ratio at about 2:1 to 2.5:1. The pressure and temperature within the reaction zone are maintained at about 1 to 4 bar gauge (barg) and about 180 to 270° C. Preferred pressure and temperature ranges are about 2 to 3.5 barg and about 180 to 260° C.

A feature of this embodiment is the removal of water of reaction along with alcohol during the esterification process. The maintenance of the alcohol:TPA mole ratio at about 2:1 to 2.5:1 requires the addition of the alcohol to the reaction vessel during the process. The alcohol/water mixture or azeotrope removed from the reaction zone may be allowed to separate into an alcohol-rich organic phase and an aqueous phase and the alcohol-rich organic phase can be returned to the reaction zone. Alternatively, the alcohol:TPA mole ratio may be maintained at about 2:1 to 2.5:1 by the addition of fresh alcohol.

The removal of water of reaction from the reaction zone is assisted by passing an inert gas through the TPA/alcohol reaction mixture in the reaction zone. Nitrogen is an example of an appropriate inert gas. The inert gas typically is fed below the surface of the TPA/alcohol reaction mixture by means of a conventional conduit or via a gas sparging device. The inert gas may be fed intermittently or discontinuously. For example, the inert gas can be fed continuously at the commencement of the esterification reaction. The amount of gas passed through the TPA/alcohol reaction mixture may vary significantly but typically is in the range of about 2 to 5 volumes of gas per volume of reaction mixture per hour.

Alcohols useful in this embodiment can include at least one of a $C_6$ to $C_{10}$ alcohol. Examples of such alcohols include hexanol, cyclohexanol, heptanol, 2-ethylhexanol (EH), cyclohexanemethanol, isomers of methylcyclohexanemethanol, octanol, nonanol, benzyl alcohol, 2-phenyl ethanol, and decanol.

Moreover, examples of the type of terephthalic acid diesters that can be produced include dihexyl terephthalate, diheptyl terephthalate, di-(2-ethylhexyl) terephthalate, dioctyl terephthalate, dibenzyl terephthalate, dinonyl terephthalate, and didecyl terephthalate.

The catalyst may be a compound soluble in the reaction mixture, i.e., soluble in the alcohol and the terephthalic acid diester product. For example, the catalyst can be a titanium catalyst. An example of suitable titanium compounds include titanium tetraalkoxides having the formula $Ti(OR)_4$ wherein R is an alkyl group of 1 to 8 carbon atoms. The catalytically-effective amount of the titanium compound generally is an amount which provides a titanium [Ti] concentration range of about 10 to 2000 parts per million by weight, 75-1000 parts per million by weight, or 100-200 parts per million by weight in the reaction mixture. The process of the present invention may be carried out in a batch, semi-continuous or continuous mode. In the batch mode, an agitated pressure vessel is charged with TPA, EH and catalyst, heated and pressurized and the esterification is carried out while passing an inert gas through the reaction mixture. An alcohol/water mixture is removed and alcohol is fed to the reaction vessel over the course of the process. At the conclusion of the process, the terephthalic acid di-ester product is recovered from the vessel and purified according to conventional procedures. Continuous operation involves continuously or intermittently feeding TPA, alcohol and catalyst to and continuously or intermittently removing alcohol, water and product-containing reaction mixture from a pressure vessel maintained at a predetermined temperature, pressure and liquid level. The product-containing reaction mixture may be fed to one or more secondary reaction vessels wherein conversion of TPA and/or TPA half-ester to the diester product is completed.

According to this embodiment, the reaction vessel may be fitted with one inlet for alcohol reactant return and a control valve to remove volatiles in lieu of a fractionation column. The reactor is charged with terephthalic acid, excess alcohol, such as 2-ethylhexanol (EH), and a catalytic amount of a titanium catalyst such as titanium tetraisopropoxide (TIPT). Heating and stirring of the mixture results in both an increase in pressure and esterification of the TPA to DOTP and the release of volatiles including EH and water. The volatile components consist primarily of the water of reaction and unreacted EH. These components can be swept out of the reactor with the aid of an inert gas purge, condensed and the 2-ethylhexanol separated from the water and returned to the autoclave via a pump. The product of this reaction typically is refined by filtering out unreacted TPA for recycle. The crude product (filtrate) is then neutralized with 2.5 weight percent aqueous NaOH, washed with water and filtered. Excess 2-ethylhexanol is stripped off at reduced pressure and the residue is then steam stripped. The stripped product is treated with activated carbon for one hour then filtered through a filter aid to give the final product.

The process according to the first embodiment, may be practiced in a continuous mode by adding the TPA to a suitable reaction vessel by means of a screw feeder and the alcohol/catalyst as a pump-fed mixture to a stirred, pressurized reaction vessel equipped with a reflux condenser/decanter combination such that the water of reaction can be removed and the unreacted alcohol returned to the reactor. The effluent from this reactor can be passed to a chain of one or more polishing reactors wherein the conversion to terephthalic acid diester with removal of water is continued. The product of this reaction can be further processed and refined by steps that are compatible with those listed for the batch example.

In another embodiment, a batch or continuous reactor can be used for the direct conversion of TPA to a terephthalic acid di-ester at normal pressure and temperature. The reactor can be a simple, stirred unit fitted with a fractionation column for water removal (and thus would not require the use of inert gas for removing water) or can contain multiple ports for reactant introduction and product removal.

For example, the reactor can be fitted with a fractionation column and access ports for charging TPA, alcohol and catalyst. The efficiency of the fractionating column can range from as many as 35 stages, to as few as two stages, but less stages results in foaming to the extent that operation of the process becomes difficult. In practice, the reactor is charged with terephthalic acid, excess alcohol, and a catalytic amount of a catalyst. Heating and stirring the mixture to reflux results in efficient removal of water and esterification of the TPA to a terephthalic acid di-ester, such as dioctyl terephthalate (DOTP), also known as di-2-ethylhexyl terephthalate. The volatile components chiefly consist of the water of reaction and unreacted alcohol. The water can be separated via a decanter, and the alcohol is allowed to reflux throughout the column. Conversion to terephthalic acid di-ester is essentially complete in six to eight hours, and the product can be filtered to remove traces of unreacted TPA for recycle. The crude product (filtrate) is then neutralized with 2.5% NaOH, washed with water and filtered. Excess alcohol is stripped off at reduced pressure. An activated carbon treatment can be employed to reduce color in the final product.

In an example of this second embodiment, the number of fractionating stages is in the range of three high-efficiency theoretical stages (HETS) to six HETS, with an exemplary number to minimize foaming in the range of four to five HETS. The amount of excess alcohol, such as 2-ethylhexanol is in the range of 25 mole percent to 40 mole percent, with an exemplary amount of 40 mole percent to facilitate conversion to diester. Unreacted alcohol can be readily recycled to the process. The process may be practiced in the continuous mode by adding the TPA to a suitable reactor by means of a screw feeder and the 2-ethylhexanol/TIPT catalyst as a pump-fed mixture to a stirred, reactor equipped with a fractionating column/decanter combination such that the water of reaction can be removed and the unreacted alcohol returned to the reactor. The effluent from this reactor can be passed to a chain of one or more finishing reactors wherein the conversion to terephthalic acid diester with removal of water is continued. The product of this reaction can be further processed and refine by steps that are compatible with those listed for the batch example.

Alcohols that can be used in this embodiment can include at least one of a $C_6$ to $C_{10}$ alcohol. Examples of such alcohols include hexanol, cyclohexanol, heptanol, 2-ethylhexanol (EH), cyclohexanemethanol, isomers of methylcyclohexanemethanol, octanol, nonanol, benzyl alcohol, 2-phenyl ethanol, and decanol. Moreover, examples of the type of terephthalic acid diesters that can be produced include dihexyl terephthalate, diheptyl terephthalate, di-(2-ethylhexyl) terephthalate, dioctyl terephthalate, dibenzyl terephthalate, dinonyl terephthalate, and didecyl terephthalate.

In this embodiment, the pressure can be maintained at about atmospheric pressure. Moreover, temperature within the reaction zone can be maintained at a range of about 150 to 270° C., with an exemplary temperature range of between about 170 to 200° C.

As with the first embodiment, the catalyst may be a compound soluble in the reaction mixture, i.e., soluble in the alcohol and the terephthalic acid diester product. For example, the catalyst can be a titanium catalyst. An example of suitable titanium compounds include titanium tetraalkoxides having the formula $Ti(OR)_4$ wherein R is an alkyl group of 1 to 8 carbon atoms. An example being tetraisopropoxytitanate which is commonly abbreviated as TIPT. The catalytically-effective amount of the titanium compound generally is an amount which provides a titanium [Ti] concentration range of about 10 to 2000 parts per million by weight, 75-1000 parts per million by weight, or 100-200 parts per million by weight in the reaction mixture. Other suitable catalysts include titanium tetrabutoxide, tin tetraethoxide, dimethyltin aceate, tin oxide, butyl stanoic acid, dibutyltin oxide, and zirconium tetraisopropoxide.

EXAMPLES

The process according to the embodiments described above is further illustrated by the following examples wherein all percentages given are by weight unless specified otherwise.

Example 1

A 500 milliliter autoclave was charged with 137.9 g (0.83 mole) TPA, 250 g (1.92 moles) EH and 125 ppm (0.048 g) TIPT catalyst. The autoclave was equipped with a stirrer, a conduit for feeding EH and nitrogen below the surface of the TPA/EH catalyst mixture, a pressure relief conduit and a conduit fitted with a control valve (backpressure regulator) for the removal of water and EH. The autoclave then was sealed and heated to approximately 180° C. to generate a pressure of 1 barg within the autoclave. As the reaction proceeded, a mixture of water and EH was removed and the EH was pumped back to the autoclave. Nitrogen was fed with the recycled EH to facilitate removal of water. Total reaction time was 10.5 hours at a maximum temperature of 260° C. and a maximum autoclave pressure of approximately 3 barg. Unreacted TPA (14 g) was recovered by filtration. The crude product then was neutralized with 2.5% aqueous NaOH, washed with water and filtered. Excess EH was stripped off at reduced pressure and the residue then steam stripped. The stripped product was treated with activated carbon at 90° C. for one hour then filtered through a filter aid to give 136.6 g of product (~80% conversion). Analysis (Gas Chromatography, area percentages): 0.04% EH; 0.07% di-(2-ethylhexyl) phthalate, 0.13% methyl (2-ethylhexyl) terephthalate; 0.02% unknown; 99.42% DOTP. Color (PCS): 20.

Example 2

A comparative experiment was performed at atmospheric pressure. To a 2-liter, round-bottom flask equipped with overhead stirrer, thermometer, heating mantel and vapor decanter was added 350 g (2.107 mol) of TPA, 687 g (5.28 mol) of EH and 0.208 g (200 ppm) of TIPT. Upon heating, the reaction began at 180° C. The temperature slowly reached 189° C. in 6 hours. A temperature of 202° C. was achieved after 10 hours reaction time. The temperature was held at about 205° C. until ~14 hours of reaction time were completed. The temperature then reached 210° C. at 15 hours, 222° C. at 18 hours and the final temperature was 230° C., where it was held for 2 hours. A reaction time of 21.5 hours was therefore required before water evolution slowed to the point that the reaction was discontinued. A total of 73.5 g of water-containing distillate was collected out of a theoretical amount of 75.8 g. The crude product was stripped of volatiles, giving a total of 125.3 g. The residue weighed 733.7 g for a yield of 88.9%. Analysis (Gas Chromatography, area percentages): 0.04% EH; 0.04% di-(2-ethylhexyl) phthalate, 0.36% DOTP Isomer; 99.39% DOTP. Color (PCS): 40.

Example 3

The reactor system and associated distillation column 20 is illustrated in FIG. 1. The equipment consisted of a one-liter base 21 fitted with a heating mantel 22, magnetic stirrer bar 23, temperature sensor 27, and distillation column 24. The attached column consisted of four sections 24a-d of all-glass, vacuum-jacketed Oldershaw columns with temperature sensors at each section 27a-d. The top of the column 24 was fitted with a head 25 to allow the water-2-ethylhexanol azeotrope to condense and collect in a decanter 26. The top 2-ethylhexanol layer was returned to the column via an overflow tube, and the water collected for weighing.

The reactor column one-liter base 21 was charged with 343.48 g (2.637 moles 25 mole % excess, MW=130.23) of 2-ethylhexanol, 1.054 mole (175 g, MW=166.13) of purified terephthalate (PTA), and 200 ppm (0.1037 g) of tetraisopropoxy titanate (TIPT). The decanter 26 was charged with 36.6 g of 2-ethylhexanol to make up for removal of the 25 mole % excess from the system otherwise. Heat-up was started, and the reaction progressed as outlined below:

| Base T | 10 Plate T | 20 Plate T | 30 Plate T | 35 Plate T | Water, g | RXN Time, h |
|---|---|---|---|---|---|---|
| 22.1 | 21.1 | 21.1 | 20.7 | 20.4 | | |
| 138.4 | 21.3 | 21.1 | 20.7 | 20.5 | | |
| 186.9 | 184.3 | 102.9 | 20.8 | 20.5 | | 0.0 |
| 187.1 | 184.7 | 182.9 | 182.1 | 182.1 | | 0.5 |
| 187.8 | 184.5 | 182.9 | 181.9 | 181.8 | | 1.0 |
| 189.5 | 184.4 | 182.6 | 181.8 | 181.5 | | 1.5 |
| 192.1 | 184.5 | 182.6 | 181.7 | 181.4 | | 2.0 |
| 191.9 | 184.4 | 182.6 | 181.6 | 181.4 | 9.8 | 2.5 |
| 196.4 | 184.0 | 181.8 | 180.7 | 179.5 | | 3.0 |
| 198.7 | 184.1 | 182.2 | 180.9 | 179.6 | | 3.5 |
| 202.8 | 184.2 | 182.4 | 181.2 | 179.9 | | 4.0 |
| 207.5 | 184.1 | 182.2 | 180.9 | 179.4 | | 4.5 |
| 213.2 | 183.8 | 181.7 | 180.6 | 181.5 | 25.3 | 5.0 |
| 231.9 | 182.8 | 180.2 | 178.8 | 176.6 | | 5.5 |
| 214.3 | 152.5 | 128.5 | 137.1 | 80.5 | 32.1 | 6.0 |
| 271.5 | 184.3 | 181.4 | 170.9 | 21.6 | | 6.5 |
| 295.8 | 185.4 | 183.3 | 182.3 | 181.0 | | 7.0 |
| 308.3 | 185.1 | 183.5 | 181.6 | 176.9 | | 7.5 |
| 307.6 | 185.2 | 183.8 | 181.0 | 169.9 | | 8.0 |
| 306.3 | 185.2 | 183.8 | 180.1 | 160.8 | 41.3 | 8.5 |
| 277.3 | 185.1 | 182.9 | 177.0 | 147.0 | | 9.0 |

Throughout the course of the reaction, no foaming was observed. The total water removed was 41.3 g. A 98.5% recovery of materials was achieved. Analysis of the crude product was as follows:

| Component, area % | 55-44-2 |
|---|---|
| -ethylhexanol | 19.81 |
| DMT | 0.03 |
| MOTP | 0.05 |
| DOTP isomer | 0.19 |
| DOTP | 78.19 |
| unknown peak @ 11.185 | 0.58 |
| Acid number, mg | 0.242 |
| KOH/g | 2 |
| calculated as % TPA | 0.036 |
| calculated as % ½ ester | 0.120 |

This material was not further processed to finished product.

Example 4

Figure 2:
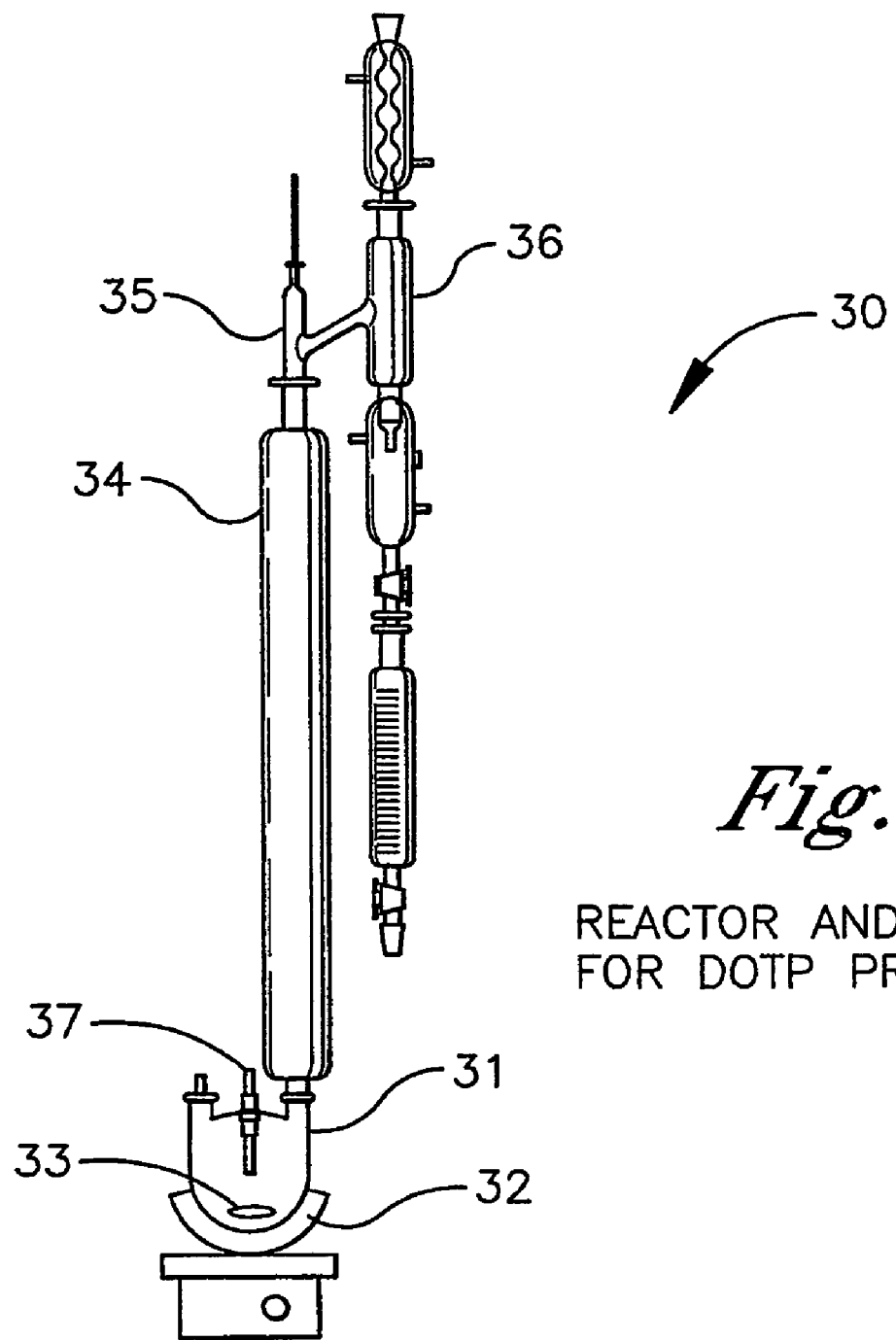
FIG. 2 shows an alternative reactor and column.

An alternative reactor/distillation configuration was constructed to test for the minimum number of stages that would provide satisfactory rates and not lead to foaming, which has been uniformly observed when insufficient fractionation is used. The modified reactor system and associated distillation column 30 is illustrated in FIG. 2. The equipment consisted of a one-liter base 31 fitted with a heating mantel 32, magnetic stirrer bar 33, temperature sensor 37, and distillation column 34. The attached column 34 consisted of a Penn-State-packed column with 10 inches of packing. The top of the column 34 was fitted with a head 35 to allow the water-2-ethylhexanol azeotrope to condense and collect in a decanter 36. The top 2-ethylhexanol layer was returned to the column via an overflow tube, and the water collected for weighing.

The one-liter base 31 was charged with 175.4 g (1.06 mole) TPA, 386.5 g (2.96 moles, 40 mole percent excess) 2-ethylhexanol and 0.2 g (355 ppm) TIPT catalyst and the mixture heated. As the reaction proceeded, water was removed via the decanter 36, and the 2-ethylhexanol returned via top overflow from the decanter 36.

| Reaction Time (hrs) | Base Temp ° C. | Take-Off Temp ° C. | Water Take-Off (g) |
|---|---|---|---|
| — | 33 | 25 | 0 |
| 0.0 | 181 | 84 | 0 |
| 0.5 | 182 | 177 | 2.5 |
| 1.0 | 183 | 177 | 1.9 |
| 2.0 | 185 | 177 | 4.3 |
| 3.0 | 187 | 178 | 4.5 |
| 4.0 | 191 | 177 | 4.8 |
| 5.0 | 195 | 176 | 5.1 |
| 6.0 | 201 | 175 | 5.6 |
| 7.0 | 212 | 173 | 6.4 |
| 7.5 | 224 | 180 | 2.7 |
| 8.0 | 225 | 182 | 0.4 |

The total water removed was 38.2 g (38.2 g theoretical). The product of this reaction was further refined to isolate finished product.

Stripping:

The 10" column was replaced column with a 3" Virgreux column to strip excess alcohol. Heat-up was started, and the stripping commenced as follows:

| Time (hrs) | Base Temp ° C. | Take-Off Temp ° C. | Vacuum, torr |
|---|---|---|---|
| 0.0 | 26 | 24 | 14 |
| 0.5 | 100 | 79 | 13 |
| 1.0 | 172 | 76 | 12 |
| 1.5 | 166 | 39 | 12 |

Neutralization, Filtering, Drying, Carbon Treating, and Filtering:

Cooled down to 90° C. and charged to a 1-Liter drop bottom flask. At 80° C. charged 150 g 2.5% NaOH, heat back to 80° C. stirring vigorously (30 min.). At temperature stopped stirring and let settle 30 minutes. Decanted and discarded the lower aqueous layer, then charged 150 g demineralized water to the pot, stirring gently and heating back to 80° C. for a water wash. Repeated this wash after decanting. Vacuum filtered the product after the water washes through a glass fiber filter circle coated with dicalite filter aid then set up filtrate for drying. Dried filtrate at 150° C. at 1 mmHg for 1.5 hours, let cool to 90° C. and charged 0.7 g carbon. Stirred at temperature for 1 hour then vacuum filtered through a glass fiber filter circle coated with dicalite filter aid. Retained filtrate as product. Wt. 350.1 g. Color (PCS): 5. Gas chromatography analysis (uncorrected area percent):

| Sample | 2-ethylhexanol | Unknown | DOTP Isomers | DOTP |
|---|---|---|---|---|
| Crude Product | 25.95% | 0.31% | 0.40% | 72.96% |
| Finished Product | 0.04% | 0.33% | 0.49% | 98.76% |

Example 5

The above-described experiment was repeated with 5" of Penn State packing rather than 10" of packing. The same quantities of materials were used. More foaming in the base was observed during this run, but was manageable if the reflux rate was controlled. Run conditions:

| Rxn. Time (hrs) | Base Temp ° C. | Take-off Temp ° C. | Take-off Vol (g) |
|---|---|---|---|
| — | 108 | 23 | — |
| 0.0 | 180 | 59 | 0 |
| 1.0 | 183 | 180 | 4.2 |
| 2.0 | 184 | 179 | 4.2 |
| 3.0 | 187 | 178 | 4.6 |
| 4.0 | 190 | 178 | 4.5 |
| 5.0 | 194 | 178 | 4.9 |
| 6.0 | 200 | 176 | 5.8 |
| 7.0 | 212 | 173 | 7.3 |
| 8.0 | 224 | 182 | 2.4 |

At total of 37.9 g of water was collected.

Stripping:

The column was replaced with a 3" Vigreux column to strip excess alcohol under the following conditions:

| Strip Time, h | Base T, ° C. | Take-off T, ° C. | Vacuum, torr |
|---|---|---|---|
| 0.0 | 25 | 24 | 13 |
| 0.5 | 25 | 24 | 13 |
| 1.5 | 113 | 82 | 14 |
| 2.0 | 157 | 72 | 14 |

Neutralization, Filtering, Drying, Carbon Treating, and Filtering:

Repeated as described in Experiment 4 to give 357.4 g of product. Analysis:

| Sample | % 2-EH | Unknown | DOTP Isomers | DOTP |
|---|---|---|---|---|
| Crude Product | 25.43% | 0.26% | 0.36% | 73.61% |
| Finished Product | 0.03% | 0.33% | 0.61% | 98.80% |

Comparative Example 6

The reaction was repeated with no column on the reactor. The decanter head was directly attached to the apparatus illustrated in FIG. 2. The same quantities of materials were used. Conditions for this run as well as comments regarding foaming were as follows:

| Rxn. Time (hrs) | Base Temp ° C. | Take-off Temp C. | Take-off vol (g) | Comments |
| --- | --- | --- | --- | --- |
| — | 64 | 24 | — | |
| 0.5 | 174 | 165 | — | Start Reaction time, water evolving; Camile output 50% |
| 1.0 | 175 | 163 | — | |
| 1.5 | 176 | 151 | 5.4 | Take-off water in X-29455-185-01 |
| 2.0 | 177 | 160 | — | Take-off temperature has surges, went from 150° C. shot to 161° C.; no foaming observed during this. |
| 2.5 | 178 | 154 | 5.6 | |
| 3.0 | 180 | 149 | — | |
| 3.5 | 182 | 163 | 5.9 | |
| 4.0 | 186 | 175 | — | Camile output to 80, get better reflux; began foaming to the top of the filter neck. |
| 4.5 | 189 | 175 | 7.1 | |
| 5.0 | 191 | 178 | 3.6 | Foaming into the joint |
| 5.5 | 196 | 178 | 4.4 | Foaming to top of the decanter @ take-off thermometer. |
| 6.5 | 204 | 173 | 3.5 | |
| | 216 | 179 | — | At 1:40 no foaming |
| 7.0 | 215 | 181 | 2.1 | 37.6 g in take-off total; no foaming except when the water is produced. |
| 7.5 | 219 | 184 | — | |
| 8.0 | 219 | 184 | — | Sampled pot as X-29455-185-02 |

Stripping and work-up were accomplished as described above to give 353.5 g of finished product. Analysis of the reaction mixture and product:

| Sample | % 2-EH | Unknown | DOTP Isomers | DOTP |
| --- | --- | --- | --- | --- |
| Crude Product | 26.43% | 0.32% | 0.39% | 72.61% |
| Finished Product | 0.28% | 0.38% | 0.58% | 98.46% |

The invention has been described in detail with particular reference to preferred embodiments thereof, but it will be understood that variations and modifications can be effected within the spirit and scope of the invention.

We claim:

1. Process for the preparation of a terephthalic acid di-ester, comprising:

contacting terephthalic acid (TPA) with at least one alcohol in the presence of a catalyst in a reactor, and removing water through a fractionation column fitted to the reactor, wherein the alcohol is a $C_6$-$C_{10}$ alcohol, the total pressure is maintained at about atmospheric pressure, the temperature is maintained at about 150° to 270° C., and the fractionation column has 3 to 35 stages.

2. The process according to claim 1, wherein the alcohol is selected from the group consisting of hexanol, heptanol, 2-ethylhexanol, octanol, nonal, and decanol and the terephthalic acid di-ester is selected from the group consisting of di-(hexyl) terephthalate, di-(heptyl) terephthalate, di-(2-ethylhexyl) terephthalate, di-(octyl) terephthalate, di-(nonyl) terephthalate, and di-(decyl) terephthalate.

3. The process according to claim 2, wherein the alcohol is 2-ethylhexanol and the terephthalic acid di-ester is di-(2-ethylhexyl) terephthalate.

4. The process according to claim 1, wherein the fractionation column has 3 to 6 stages.

5. The process according to claim 1, wherein the catalyst is a titanium catalyst.

6. The process according to claim 5, wherein the titanium catalyst is a titanium tetraalkoxide having the formula $Ti(OR)_4$ wherein R is an alkyl group of 1 to 8 carbon atoms.

7. Process according to claim 6, wherein the titanium tetraalkoxide catalyst has the formula $Ti(OR)_4$ wherein R is an alkyl group of 1 to 8 carbon atoms and the concentration of the catalyst in the reaction mixture is an amounts which provides a titanium [Ti] concentration of about 50 to 200 parts per million by weight.

* * * * *